United States Patent [19]

Taylor

[11]  4,175,128
[45]  Nov. 20, 1979

[54] METHOD FOR TREATING CONGESTIVE HEART FAILURE

[75] Inventor: Colin R. Taylor, Waterford, Conn.

[73] Assignee: Pfizer Inc., New York, N.Y.

[21] Appl. No.: 986

[22] Filed: Jan. 3, 1979

[51] Int. Cl.$^2$ .......................... A61J 3/06; A61J 3/07; A61J 3/10; A61K 31/44

[52] U.S. Cl. .................................. 424/263; 424/14; 424/45; 424/46

[58] Field of Search ...................... 424/263, 14, 45, 46

[56] References Cited

U.S. PATENT DOCUMENTS

| 3,700,681 | 10/1972 | Barth | 424/263 X |
| 3,948,919 | 4/1976 | Nakanishi | 424/263 X |
| 4,053,605 | 10/1977 | Baldwin | 424/263 |
| 4,061,756 | 12/1977 | Hastings et al. | 424/263 |

OTHER PUBLICATIONS

Willey et al, Br. J. Clin. Pharmac., 1976, (3) pp. 595-600.
British J. Clin. Pharmac., 1977, 4, 376-377.
Stephens et al, Br. J. Clin. Pharmac., 1978, 6, pp. 163-170.
Wilson et al, Brit. Heart Jour., 1977, 39, pp. 721-725.

Primary Examiner—Dale R. Ore
Attorney, Agent, or Firm—Connolly and Hutz

[57]  ABSTRACT

A method for the treatment of congestive heart failure in humans using pirbuterol or pharmaceutically acceptable acid addition salts thereof.

7 Claims, No Drawings

METHOD FOR TREATING CONGESTIVE HEART FAILURE

BACKGROUND OF THE INVENTION

1. Field of the Invention

This invention relates to the use of pirbuterol, a known sympathomimetic amine of the formula

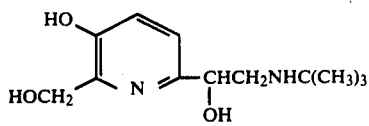

and the pharmaceutically acceptable acid addition salts thereof in treating congestive heart failure.

2. Description of the Prior Art

Congestive heart failure, regardless of its etiology, is characterized by a distention of the myocardial tissue of the left and/or right ventricles of the heart reducing the efficiency with which the blood is ejected into systemic and/or pulmonary circulations and results in elevated venous pressure, lowered cardiac output and peripheral and pulmonary edema. If left untreated the health of a patient with congestive heart failure could deteriorate to the point where the disease would be fatal.

While there are several medicinals available for the treatment of congestive heart failure, the most widely used is digitalis. Although digitalis is moderately effective in the treatment of this disease, its use is limited because of its slow onset of action and the small difference between the maximum therapeutic and minimum toxic dose levels.

SUMMARY OF THE INVENTION

A method has now been found for treating congestive heart failure in a human subject having such condition which comprises administering orally, parenterally or by inhalation to said human subject a congestive heart failure treating amount of a compound of the formula

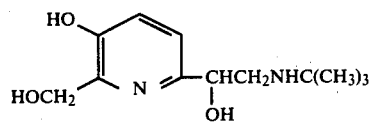

or a pharmaceutically acceptable acid addition salt thereof. Especially preferred acid addition salts are the dihydrochloride salt and monoacetate salt of the compound of formula (I). The compounds of the invention cause major improvement in key hemodynamic parameters associated with relief of congestive heart failure.

DETAILED DESCRIPTION OF THE INVENTION

As previously mentioned, the compounds of the present invention are known in the art. 2-Hydroxymethyl-3-hydroxy-2-(1-hydroxy-2-t-butylaminoethyl)pyridine of the formula (I) and its pharmaceutically acceptable acid addition salts are claimed in U.S. Pat. No. 3,700,681. The free base of formula (I) is known in the art by the generic name "pirbuterol." An especially preferred compound of the invention is the dihydrochloride salt of the compound of formula (I) known generically as pirbuterol dihydrochloride, a bronchodilating agent useful in treatment of asthma upon oral administration or by inhalation therapy. See, for example, Paterson et al., *Brit. J. Clin. Pharmacol.*, 4, 376 (1977); Willey et al., ibid., 3, 595 (1976); Brandon, *Annals of Allergy*, 39, 117 (1977) and Steen et al., *Research on: Clinical Pharmacology and Therapeutics, Respiratory System*, 2, 1623 (1974). Another especially preferred compound of the invention is the monoacetate of the compound of formula (I), known generically as pirbuterol acetate.

As mentioned above the present method of the invention embraces the compounds of formula (I) and pharmaceutically acceptable acid addition salts thereof. Included in such salts are the mono- and diacid addition salts of the compounds of formula (I) each of which can be prepared by methods known in the art, see e.g., U.S. Pat. Nos. 3,700,681 and 3,948,919. Besides the especially preferred dihydrochloride salt, other examples of mono- and diacid addition salts include the hydrobromide, hydroiodide, nitrate, sulfate, sulfite, phosphonate, phosphate, acetate, lactate, citrate, tartarate, succinate, maleate, glutarate, gluconate, propionate, caproate, laurate, stearate and phenylacetate salts.

As is obvious to one skilled in the art, compounds of the instant invention contain an asymmetric atom at the site of the carbinol carbon atom on the amine bearing side chain. The present invention includes the racemate and enantiomers of formula (I). Resolution of the racemate into the optically active isomers (enantiomers) can be carried out by methods familiar to those skilled in the art and which are reviewed in Gelman, "Organic Chemistry—An Advance Treatise," J. Wiley and Sons, Inc., New York, N.Y., 1953, Vol. I, page 214ff.

For treating patients suffering from congestive heart failure the compounds of the invention may be administered either as individual therapeutic agents or as mixtures of therapeutic agents. They may be administered alone, but are generally administered with a pharmaceutical carrier selected on the basis of the chosen route of administration and standard pharmaceutical practice. For example, they may be combined with various pharmaceutically acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various nontoxic organic solvents. Moreover, the oral pharmaceutical compositions of this invention may be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of the standard pharmaceutical practice. For example, where the instant compounds are administered orally in tablet form, excipients such as lactose, sodium citrate, calcium carbonate and dicalcium phosphate may be used. Various disintegrants such as starch, alginic acids, and certain complex silicates, together with lubricating agents such as magnesium stearate, sodium lauryl sulphate and talc, may also be used in producing tablets for the oral administration of these compounds. For oral administration in capsule form, lactose and high molecular weight polyethylene glycols are among the preferred materials for use as pharmaceutically acceptable carriers. Where aqueous suspensions are to be used for oral administration, the compounds of this invention may be combined with emulsifying or suspending agents. Diluents such as ethanol, propylene glycol, glycerine and their combinations may be employed as well as other materials.

For purposes of parenteral administration and inhalation, solutions or suspensions of the instant compounds in sesame or peanut oil or in aqueous propylene glycol solutions can be employed, as well as sterile aqueous solutions of the soluble acid addition salts described herein. These particular solutions are especially suited for intramuscular and subcutaneous injection purposes. The aqueous solutions, including those of the acid addition salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

Pirbuterol or its pharmaceutically acceptable salts may be administered to subjects suffering from congestive heart failure by means of inhalators or other devices which permit the active compounds to come into direct contact with the respiratory tract of the subject. When administered by inhalation, the compounds can comprise (1) a solution or suspension of the active ingredient in a liquid medium of the type mentioned above for administration via a nebulizer; (2) a suspension or solution of the active ingredient in a liquid propellant such as dichlorodifluoromethane or chlorotrifluoroethane for administration from a pressurized container; or (3) a mixture of the active ingredient and a solid diluent (e.g. lactose) for administration from a powder inhalation device. Compositions suitable for inhalation by means of a conventional nebulizer will comprise about 0.1 to about 0.5% of active ingredient; and those for use in pressurized containers will comprise from about 0.5 to about 5% of active ingredient. Compositions for use as powder inhalants will comprise ratios of active ingredient to diluent of from about 1:0.5 to about 1:1.5. When administered by means of a spray formulated as a solution in an aqueous or nonaqueous solvent, e.g., propellants such as fluorinated hydrocarbons, utilization several times a day is preferred. For such application, a halogenated hydrocarbon propellant of up to 2 carbon atoms is employed. The propellant may be any of the conventional propellants used in aerosol formulations, for example halogenated hydrocarbons of the fluorohydrocarbon or fluorohalohydrocarbon type such as trichloromonofluoromethane, dichlorodifluoromethane, dichlorotetrafluoroethane, monochlorotrifluoromethane, monochlorodifluoromethane and mixtures of any of these together or with other propellants. Typical of suitable propellants are those disclosed in, for example, U.S. Pat. No. 2,868,691 and sold under the trademark Freon.

It is necessary that the active ingredient form a proportion of the composition such that a suitable dosage form will be obtained. Obviously, several dosage unit forms may be administered at about the same time. Although compositions with less than 0.01 percent by weight of active ingredient might be used in certain instances, it is preferred to use compositions containing not less than 0.01 percent of the active ingredient; otherwise the amount of carrier becomes excessively large. Activity increases with the concentration of the active ingredient. The composition may contain 10, 50, 75, 95 or an even higher percentage by weight of the active ingredient.

Obviously, the physician will ultimately determine the dosage which will be most suitable for a particular individual, and it will vary with the age, weight and response of the particular patient as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a small quantity administered parenterally.

For routine treatment of ambulatory patients suffering from congestive heart failure by the instant method it is generally preferred to administer pirbuterol or a pharmaceutically acceptable acid addition salt thereof by the oral route. When the compounds of the invention are administered orally, a daily dosage of from about 15 to 90 mg. is therapeutically effective and dosages of 20 to 60 mg. per day administered in increments of 10 to 20 mg. are preferred.

Parenteral administration, especially by the intravenous route, is recommended for hospitalized patients suffering from acute congestive heart failure, particularly such patients suffering from life-threatening exacerbations of heart failure. When administered parenterally an effective dosage is from about 3 to 30 mg. per day with a preferred range of about 3 to 10 mg. per day in single or divided doses. Intravenous dosages are preferable given by injection.

Administration of the compounds of the invention by inhalation is indicated for administration in episodes of acute paroxysmal nocturnal dyspnea. When administered in this manner the effective daily dosage and preferred range are the same as set forth above for parenteral administration.

The above values are illustrative, and there may, of course, be individual cases in which higher or lower dose ranges are merited.

The following examples are provided to illustrate the method of the invention.

EXAMPLE 1

The following study was carried out to determine the effects of orally administered pirbuterol dihydrochloride in patients with congestive heart failure.

The study comprised five patients, four females and one male, mean age 56 years (range 38 to 73 years) each of whom showed evidence of congestive heart failure documented by radiologically confirmed cardiomegaly and pulmonary vascular congestion within one week prior to the study, pulmonary wedge pressure of at least 15 mm. Hg. immediately prior to pirbuterol administration and physical findings of congestive heart failure. Four of the patients were functional Class III by the New York Heart Association Classification (Committee on Exercise, American Heart Assoc. Exercise Testing and Training: Handbook for Physicians, New York, 1972). The remaining patient was functional Class I. The cause of heart failure for each patient was either ischaemic heart disease, idiopathic or alcoholic cardiomyopathy, chronic mitral regurgitation or chronic aortic regurgitation.

Physical examination was performed, and a medical history and informed consent for the study was obtained for each patient. All patients were receiving digitalis and diuretic therapy prior to the trial. However, these medications were withheld at least 12 hours prior to the study until six hours following the last dose of pirbuterol dihydrochloride. The selected patients were not using antihypertensive drugs, inotropic or chronotropic drugs, drugs affecting vascular resistance or another investigational drug. They were free of other major diseases including hyperthyroidism and diabetes mellitus. Patients having supine or standing blood pressure less than 100 mm. Hg systolic or 60 mm. Hg diastolic or greater than 95 mm. Hg diastolic were excluded from the study as were those having unstable angina pectoris or myocardial infarction within the previous three months.

Hemodynamic parameters were obtained prior to and following dosing with pirbuterol dihydrochloride. Patients were under constant observation for at least five hours following dosing. A Swan-Ganz catheter [Ganz et al., Am. J. Cardiol. 29, 241 (1972)] and intra-arterial line was inserted into each patient in the cardiac catherization laboratory after which they were transferred to a room equipped with intensive monitoring devices. The following parameters were measured in the supine position 15 minutes and immediately prior to the first dose of pirbuterol dihydrochloride, at 1, 2, 3, 4 and 5 hours after the first dose and at 1, 2, 3, 4 and 5 hours after the second dose:

Cardiac Index
Pulmonary wedge pressure (PWP)
Total systemic vascular resistance (TSVR)
Total pulmonary vascular resistance (PVR)
Mean systemic arterial blood pressure (MAP)
Right atrial pressure (RAP)
Heart rate The results obtained after the first oral dose of pirbuterol dihydrochloride is summarized in Table I, below.

response to the treatment with pirbuterol. Reduction in pulmonary wedge pressure (PWP, also known as left ventricular filling pressure) and reduction in arterial pressure have been shown by Franciosa et al., Circulation, 50, 1020 (1974) to be important parameters in ascertaining the efficacy of drugs in treatment of congestive heart failure. In the present study the average peak reduction in PWP was 36% with a range of 13.3 to 51.2%. The mean arterial blood pressure showed an average reduction of 9.8% (range 3.1 to 17.7%). The mean decrease in right atrial pressure (RAP) for all patients was 43.6%, a marked decrease especially in view of the fact that the NYHA functional Class I patient (No. 2), who was found to have a low predosing RAP, showed no effect in this parameter. The importance of improved cardiac output and decreased vascular impedence in management of congestive heart failure is known in the art, see e.g., Cohn, Amer. J. Med., 55, 351 (1973). These parameters are improved very appreciably by pirbuterol. As shown in Table I the mean peak increase in cardiac index was 40.1% while the total systemic vascular resistance (TSVR) and pulmonary vascular resistance were reduced in the patients by averages of 30.4% and 48.5%, respectively.

When a second dose of pirbuterol dihydrochloride is administered to the patients similar results are obtained.

Administration of an aerosol dosage form of pirbuterol acetate at levels of 3 to 10 mg. per day by inhalation and by intravenous injection at the same level of drug also gives comparable results.

EXAMPLE 2

Tablets

A tablet base is prepared by blending the following ingredients in the proportion by weight indicated:

Sucrose U.S.P.—80.3

TABLE I

Effects of First Oral Dose of Pirbuterol . 2HCl in Patients with Congestive Heart Failure*

| Patient Number | Age (Yrs) | Sex | NYHA Funct. Class | Cardiac Index Bl | Cardiac Index %↑ | Pulmonary Wedge Pressure Bl | Pulmonary Wedge Pressure %↓ | TSVR Bl | TSVR %↓ | PVR Bl | PVR %↓ | MAP Bl | MAP %↓ | RAP Bl | RAP %↓ | Heart Rate Bl | Heart Rate %↑ | Dose (mg) |
|---|---|---|---|---|---|---|---|---|---|---|---|---|---|---|---|---|---|---|
| 1 | 70 | F | III | 1.45 | 17.2 | 15 | 13.3 | 3042 | 17.6 | 337 | 41.5 | 99 | 9.1 | 13.3 | 47.4 | 98 | 4.1 | 5 |
| 2 | 38 | F | I | 2.65 | 18.9 | 20.5 | 51.2 | 1144 | 19.2 | 61.7 | 57.9 | 87.5 | 17.7 | 4.5 | 0 | 73.5 | 11.6 | 10 |
| 3 | 73 | F | III | 1.55 | 61.3 | 26 | 30.8 | 1785 | 44.4 | 408 | 41.2 | 63.5 | 5.5 | 11 | 45.5 | 89 | 4.5 | 15 |
| 4 | 46 | F | III | 2.4 | 54.2 | 17 | 47.1 | 1327 | 45.5 | 200 | 61 | 87 | 13.8 | 8.5 | 52.9 | 87.5 | 8.6 | 15 |
| 5 | 55 | M | III | 2.55 | 49.0 | 22.5 | 37.8 | 1071 | 25.4 | 146 | 41.1 | 80.5 | 3.1 | 14.5 | 72.4 | 75 | 8.0 | 20 |
| Means | 56.4 | 4-F 1-M | I-III | 2.12 | 40.1 | 20.2 | 36.04 | 1674 | 30.4 | 231 | 48.5 | 83.5 | 9.8 | 10.4 | 43.6 | 84.6 | 7.4 | 13 |

*Cardiac Index is expressed as liters minutes$^{-1}$ meters$^{-2}$,
Pulmonary wedge pressure, millimeter of mercury,
TSVR = Total systemic vascular resistance, dynes seconds centimeters$^{-5}$,
PVR = Total pulmonary vascular resistance, dynes seconds centimeters$^{-5}$,
MAP = Mean systemic arterial blood pressure, millimeters of mercury,
RAP = Right atrial pressure, millimeters of mercury,
Heart rate    ats per minute,
Bl = Bas...  value, the average of the two predosing values,
% ↑ or ↓   = Peak increase (↑) or decrease (↓) post dosing (usually 2-4 hours), percent.

In each of the patients the hemodynamic parameters showed marked improvement. Although heart rate increased somewhat, the increase is not considered excessive and is quite comparable to that reported for sodium nitroprusside, a preferred drug for use after cardiac surgery, by Poole-Wilson et al., Brit. Heart J., 39 721 (1977). In the same reference, salbutamol, 2-(t-butylamino)-1-(4-hydroxy-3-hydroxymethylphenyl)ethanol, was found to cause significantly greater increase in heart rate.

The average peak improvement in the other hemodynamic parameters indicates a very favorable overall Tapioca starch—13.2
Magnesium stearate—6.5
Into this tablet base is blended sufficient 2-hydroxymethyl-3-hydroxy-6-(1-hydroxy-2-t-butylaminoethyl)pyridine (pirbuterol) to provide tablets containing 5, 10, 20 and 50 mg. of active ingredient per tablet. The compositions are each pressed into tablets, each weighing 360 mg., by conventional means.

EXAMPLE 3

Capsules

A blend is prepared containing the following ingredients in proportion by weight indicated below:
- Calcium carbonate, U.S.P.—17.6
- Dicalcium phosphate—18.8
- Magnesium trisilicate, U.S.P.—5.2
- Lactose, U.S.P.—5.2
- Potato starch—5.2
- Magnesium stearate A—0.8
- Magnesium stearate B—0.35

To this blend is added sufficient pirbuterol dihydrochloride to provide capsules containing 5, 10, 20 and 30 mg. of active ingredient per capsule. The compositions are filled into hard gelatin capsules in the amount of 350 mg. per capsule.

EXAMPLE 4

Injectable Preparation

Pirbuterol acetate, 1000 g., is intimately mixed and ground with 2,500 g. of sodium ascorbate. The ground dry mixture is placed in vials and sterilized with ethylene oxide after which the vials are sterilely stopped. For intravenous administration, sufficient sterile water is added to the materials in the vials to form a solution containing 1.0 mg. of active ingredient per milliliter of injectable solution.

EXAMPLE 5

Parenteral Solution

A solution of pirbuterol dihydrochloride is prepared with the following composition:
- Effective ingredient—6.04 g.
- Magnesium chloride.6H$_2$O—12.36 g.
- Monoethanolamine—8.85 ml.
- Propylene glycol—376.00 g.
- Distilled water—94.00 ml.

The resulting solution has a concentration of effective ingredient of 10 mg./ml. and is suitable for parenteral administration.

EXAMPLE 6

Suspension

A suspension of pirbuterol dihydrochloride is prepared having the following composition:
- Effective ingredient—25.00 g.
- 70% aqueous sorbitol—741.290 g.
- Glycerin, U.S.P.—185.350 g.
- Gum acacia (10% solution)—100.000 ml.
- Polyvinylpyrrolidone—0.500 g.
- Distilled water—to make one liter Various sweeteners and flavorants are added to this suspension to improve its palatability. The suspension contains approximately 25 mg. of effective ingredient per milliliter.

EXAMPLE 7

Aerosol

An aerosol composition of pirbuterol acetate is prepared containing:
- pirbuterol acetate—0.6 g.
- Freon* 115/Freon* 114 (40/60 w/w)—65.4 g.
- Ethyl alcohol—34 g.

*Registered Trademark.

The pirbuterol is added to the ethyl alcohol and the mixture placed into a plastic coated aerosol bottle. The bottle is charged with the propellant and then sealed with a metering device designed to meter 0.2 gram per dose, equivalent to 1.0 mg. of pirbuterol.

EXAMPLE A

Pirbuterol Acid Addition Salts

The general procedure comprises adding pirbuterol in ethanol to a solution of an excess (20%) of the appropriate acid in a suitable solvent. The salts are precipitated by addition, if necessary, of a solvent in which the salt is insoluble (non-solvent), and chilling of the mixture.

| Acid | Solvent | Non-Solvent | M.P.(°C.) | C | H | N | C | H | N |
|---|---|---|---|---|---|---|---|---|---|
| acetic | C$_2$H$_5$OH | (CH$_3$)$_2$CO | 157-9 (dec.) | 55.98 | 8.05 | 9.08 | 56.06 | 8.15 | 9.08 |
| propionic | C$_2$H$_5$OH | (i-C$_3$H$_7$)$_2$O | 141-2.5 | 57.30 | 8.34 | 8.91 | 57.53 | 8.38 | 8.88 |
| phenylacetic | C$_2$H$_5$OH | (CH$_3$)$_2$CO | 166.5-8 | 63.81 | 7.50 | 7.44 | 63.56 | 7.64 | 7.18 |
| nonanoic | (C$_2$H$_5$)$_2$O | — | 131.5-2.5 | 63.28 | 9.54 | 7.03 | 62.93 | 9.45 | 7.02 |
| decanoic | (C$_2$H$_5$)$_2$O | — | 124-5 | 64.04 | 9.74 | 6.79 | 63.73 | 9.40 | 6.37 |
| lauric | (C$_2$H$_5$)$_2$O | — | 120.5-4 | 65.42 | 10.06 | 6.36 | 65.52 | 9.82 | 6.07 |
| palmitic | (C$_2$H$_5$)$_2$O | — | 121.5-2.5 | 67.70 | 10.55 | 5.64 | 67.92 | 10.52 | 5.30 |
| stearic | C$_2$H$_5$OH | (CH$_3$)$_2$CO | 125.5-6.5 | 68.66 | 10.76 | 5.34 | 68.79 | 10.79 | 5.24 |
| glutaric | C$_2$H$_5$OH | (CH$_3$)$_2$CO | 158-60 | 56.84 | 7.90 | 9.14 | 57.08 | 7.86 | 9.15 |
| sulfuric* | C$_2$H$_5$OH | (CH$_3$)$_2$CO | 198 | 42.59 | 6.55 | 8.28 | 42.65 | 6.48 | 8.51 |

*A 100% excess of sulfuric acid is used. The addition of acetone forms a gum which is separated by decantation of the solvent. It is stirred overnight in ether and the resulting solid recrystallized from N,N-dimethylformamide-isopropyl ether.

What is claimed is:

1. A method of treating congestive heart failure in a human subject having such condition which comprises administering orally, parenterally or by inhalation to said human subject a congestive heart failure treating amount of a compound of the formula:

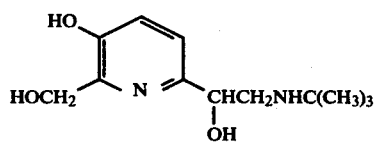

or a pharmaceutically acceptable acid addition salt thereof.

2. The method according to claim 1 wherein said compound is administered orally.

3. The method according to claim 1 wherein said compound is administered parenterally.

4. The method according to claim 3 wherein said parenteral administration is intravenous.

5. The method according to claim 1 wherein said compound is administered by inhalation.

6. The method according to claim 1 wherein said acid addition salt is the dihydrochloride.

7. The method according to claim 1 wherein said acid addition salt is the monoacetate.

* * * * *